United States Patent [19]

Ledergerber

[11] Patent Number: 5,354,338
[45] Date of Patent: Oct. 11, 1994

[54] TEXTURIZED COVERING FOR IMPLANTS

[76] Inventor: Walter J. Ledergerber, 31 Morningwood, Laguna Niguel, Calif. 92677

[21] Appl. No.: 660,291

[22] Filed: Feb. 22, 1991

[51] Int. Cl.$^5$ ............................................. A61F 2/12
[52] U.S. Cl. .................................. 623/8; 623/66; 264/225
[58] Field of Search ............ 623/8.66, 1, 11, 12; 264/226, 212, 1.1, 2.5, 220, 225; 600/36

[56] References Cited

U.S. PATENT DOCUMENTS

| | | | |
|---|---|---|---|
| 3,365,524 | 1/1968 | Thompson et al. | 264/226 |
| 3,387,351 | 6/1968 | Roosen | 264/220 |
| 3,548,041 | 12/1970 | Steding | 264/225 |
| 3,632,695 | 1/1972 | Howell | 264/2.5 |
| 3,718,078 | 2/1973 | Plummer | 264/2.5 |
| 4,278,630 | 7/1981 | Scheicher | 264/225 |
| 4,329,385 | 5/1982 | Banks et al. | 264/220 |
| 4,576,850 | 3/1986 | Martens | 264/1.1 |

*Primary Examiner*—David Isabella
*Attorney, Agent, or Firm*—Lyon & Lyon

[57] ABSTRACT

Methods for manufacturing texturized coverings for implants into the human body are described which generate small wells or channels on the exterior surface of the implant. Optionally, the texturized surface may be formed by affixing globules on the exterior surface of a mandrel or the interior surface of a mold, which is then coated with silicone rubber and cured. The surface may be optionally microtexturized, for example, by microtexturizing the surface of the globules by etching or sand blasting.

6 Claims, 1 Drawing Sheet

TEXTURIZED COVERING FOR IMPLANTS

FIELD OF THE INVENTION

This invention relates generally to coverings for implants into the human body. More particularly, the invention relates to texturized coverings, including microtexturized coverings, for implants for use within the human body.

BACKGROUND OF THE INVENTION

Implantable prosthetic devices have been used in numerous locations in the body. The most common use has been for restoring or improving upon normal body contour or augmenting as well as reconstructing the female breast. The most common breast prosthesis is similar to that disclosed in U.S. Pat. No. 3,293,663 to Cronin, in which there is a flexible elastomeric container, typically silicone rubber, which is filled with a soft gel, typically silicone gel or a saline solution or a combination of both.

It is known that when a prosthetic device, including the Cronin type device, is implanted in the body, scar tissue totally encapsulates the device. This encapsulation leads to a problem of spherical scar contracture. As the scar tissue surrounds the prosthetic device it tends to contract, thereby causing the gel filled sac to assume a minimum surface area to volume configuration or spherical configuration. The problem of spherical scar contracture causes the breast implant to change from a shape approximating that of a natural human breast to that of a tennis ball.

Numerous solutions to the spherical scar contracture problem have been posed. A number of essentially structural and mechanically oriented devices have been proposed for amelionation of this problem. A number of these references are reviewed in the Background of the Invention section of my U.S. Pat. No. 4,955,907, the disclosure of which is incorporated herein by reference. Generally, these structural/mechanical approaches have proved unsatisfactory.

More recently, the use of a covering for implants having a plurality of defined regions which serve to disperse or disorganize the scar tissue have been disclosed. For example, in my U.S. Pat. No. 4,955,907, a variety of embodiments are disclosed which promote the dispersion or disorganization of scar tissue, among other ways, by providing defined boundaries for such tissue. It has been recognized that utilizing covering materials having highly and variables texturized surface, including microtexturized surface, promotes enhanced fixation of tissues to the implant, while reducing the region over which the undesirable scar tissue may pool and form.

A number of references have suggested various techniques for generating a texturized or microtexturized surface for the covering of the implant. One technique, described for example in Ersek et al, U.S. Pat. No. 4,944,909, is to include specific molecules whose shape and size produce 3-dimensional projections of from 20 to 500 microns in size from the exterior surface of the covering for the implant. Prior to vulcanization of the silicone rubber covering, the molecules are thrust onto the exterior surface with sufficient force to alter the surface morphology. A second technique is described in Patents to Cox U.S. Pat. No. 4,859,712 and Quaid U.S. Pat. 4,889,744. Both references disclose a technique of manufacturing texturized silicone rubber surfaces by applying particles or crystals to the external surface of the implant before it is cured, curing the external surface layer with those solid particles or crystals embedded in the surface, and then dissolving the crystals or particles with a solvent which does not dissolve the silicone rubber. A third set of techniques is disclosed in Yan et al U.S. Pat. No. 4,960,425. Generally a number of the disclosed techniques relate to the use of covering a silicone rubber layer with a porous or textured medium and pressing that medium into the silicone rubber until a texturized surface is formed in the silicone layer. Embodiments are described where the silicone rubber is in a disk form and where the silicone rubber surrounds a mandrel. An additional embodiment is described in which a mandrel has a texturized surface over which the silicone rubber is placed and cured. In yet another embodiment, the surface is scratched, carved, burned, or etched using ion beam, chemical or other physical techniques to texturize the exterior surface. There is no specific disclosure in the prior art of texturizing material for coating the mandrel or inside of a mold cavity to generate a texturized surface of the exterior of the implant.

SUMMARY OF THE INVENTION

A covering for an implant has small wells or channels on the exterior surface of the covering. In the preferred embodiment, the small wells or channels may further have microtextured surfaces. The small wells or channels serve to limit pooling of biologic fluids, such as collagen, on the implant covering, thereby reducing the effects of scar contracture, and provide for greatly increased surface area which serves to enhance affixation of tissues to the implant, identical in its operative effort to the nested polygonal ("hexcel") structures identified as FIG. 11 in my U.S. Pat. No. 4,955,907.

The preferred method of manufacturing the textured coating consists of attaching, preferably by sintering or gluing, texturized materials consisting of substantially spherical globules onto the exterior surface of a mandrel or the interior surface of a mold. Alternatively, the texturized surface may be molded as part of a molded mandrel or otherwise machined. The globules may be further microtexturized by, for example but not limited to, sand blasting, etching, electrical discharge machining or ultrasonic impact machining. Another embodiment of manufacturing the texturized coating of this invention consists of the inclusion of nonsoluble materials within the silicone rubber film, followed by removal of the inclusions such as by ultrasonic vibra-cleaning. In yet a third embodiment of the method of manufacturing the coverings of this invention, the surface of the silicone rubber is distressed such as by gas jet impact distressing, imprint distressing or abrasion distressing techniques. In a fourth embodiment for manufacturing the surface of this invention, an implant surface is texturized by affixing filaments to the surface upon which liquid silicone rubber is applied, thereby resulting in a texturized coating. In a final embodiment of the method of manufacturing the surface of this invention, a silicone rubber foam is formed by injecting electrically charged gas bubbles into liquid silicone rubber, wherein those bubbles may be located at the desired location within the rubber by application of an electric field.

Accordingly, it is a principal object of this invention to provide useful methods for manufacture of a texturized coating for an implant.

It is a further object of this invention to provide useful techniques for microtexturizing the surface of an implant.

DETAILED DESCRIPTION OF THE INVENTION

Figure 1:
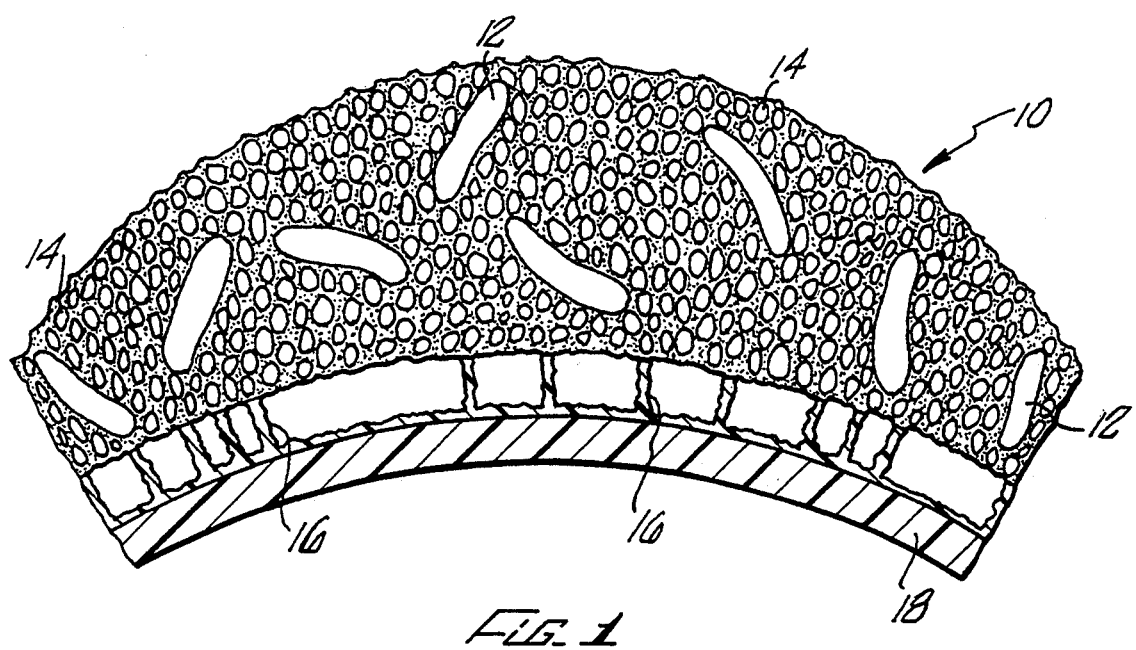
FIG. 1 is a cross-sectional and perspective view of the surface showing small wells or channels.

FIG. 1 shows a perspective view of the texturized coating for an implant of this invention, with the foremost portion being shown in cross-section. The implant covering 10 has a plurality of channels 12 and small wells 14. The surface of the channels 12 and wells 14 may be microtexturized on the face of the well or channel 16. The channels 12 and wells 14 are typically random in shape, though a more regular shape is also consistent with the objects and teachings of this invention. The covering 10 may be backed by a backing 18, such as a bonded silicone elastomer barrier layer. This texturing, with optional microtexturing, may be disposed on any or all of the surface of the implant. The purpose of these channels 12 and wells 14 is to a) limit pooling of biologic fluids on a limited portion of the implant covering, and b) to provide for greatly increased surface area which serves to enhance affixation of tissues to the implant.

METHODS OF MANUFACTURING THE TEXTURIZED COVERING

Affixing Texturizing Materials to a Mandrel or Mold

The texturized coating 10 may be manufactured by affixing, preferably by sintering or gluing, substantially spherical globules onto a mandrel or on the inside of a mold surface. In the case of a mandrel, the mandrel is then dipped into liquid silicone rubber allowing for the build up of the silicone rubber covering structure which is then vulcanized. In the case of a mold, the inner surface of the mold is covered with the globules, producing a molded part with a texturized surface.

The globules may be of any suitable material for the stated purposes, and preferably are metal, plastic or glass. Materials suitable for sintering and gluing include gold, platinum, tin, aluminum, brass, bronze, pyrex or any other material known to those skilled in the art of molding and mold manufacture.

The globules may be further texturized, resulting in microtexturization, by techniques including, but not limited to, sand blasting, etching, electrical discharge machining, ultrasonic impact machining, heat treating, super-cooled treating, laser machining, fracturing, ion beam distressing, or any other suitable technique. Additionally, chemical leaching of calcareous or other leachable inclusions incorporated into the globules utilized for the manufacturing of the coverings may be used.

Inclusion Impregnated Film Followed By Chemical Leaching and/or Ultrasonic Cleaning The texturized coating of this invention may be manufactured by applying a coating such as by dusting or flocking onto a molded or dipped silicone rubber shell having a partially cured outer surface with particles such as calcium carbonate dust, silicon dust, or other materials followed by vulcanization or other curing of the rubber. After curing, the inclusions are removed by chemical leaching, ultrasonic vibra cleaning or a combination of both, to remove the included materials from the surface.

Silicon Rubber Microfragments and Microfilaments

In one method of manufacturing the texturized and microtexturized covering of this invention, silicone rubber and other plastic polymer microfragments and microfilaments may be affixed to the unvulcanized surface of the implant. In this technique, partially cured microfragments and microfilaments of the silicone rubber or other plastic polymers are applied by dusting or spraying onto the uncured silicone, which is then vulcanized or otherwise cured. The resulting structure is a microtexturized surface whose topographical characteristics are largely controlled by selection of microfragments and microfilament size and cure rate. Optionally, the covering may be further treated by coating with liquid silicone polymers.

As a slight variant on this method, a slurry made of silicone rubber microfragments and microfilaments suspended in liquid silicone rubber may be used to coat the implant coverings. After application, the technique remains as described previously.

Distressing of Silicone Rubber Surface

The texturized coverings of this invention may be manufactured by distressing the exterior surface of the covering. In one preferred embodiment, a focused gas jet impact-distresses the unvulcanized or partially cured silicone rubber. In another embodiment, laser machining of the surface of the implant may be used. In these ways, a texturized and microtexturized coating may be formed.

Alternatively, imprint distressing utilizing a microtexturized roller may be utilized to imprint an unvulcanized silicone rubber sheet. An imprinting roller may be utilized optionally on a sheet of material to be utilized on the exterior of the implant, or upon the covering itself mounted on a mandrel or stretched as a sheet. The imprinting pressure must be regulated to provide optimal texturization. After imprinting and partially curing, the covering is vulcanized or otherwise cured.

Plastic Filament Onlay Texturizing

Figure 2:
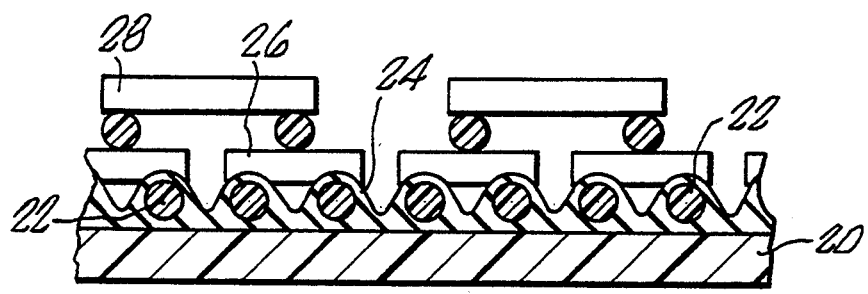
FIG. 2 is a cross-sectional view of a covering constructed according to the plastic filament onlay texturizing method.

FIG. 2 shows a structure resulting from a plastic filament onlay texturizing method. A backing material 20 supports filaments 22 which are then covered with liquid silicone rubber 24. The filaments 22 may be Dacron, PTFe filaments or other plastic filaments including silicone rubber. The filaments 22 may be at one level, or alternatively, wound upon the first level filament 22 to form second level filaments 26 or higher level filaments 28. The filament covered surface 20 may then be dipped or sprayed with liquid silicone rubber resulting in a scaffold like structure for the liquid silicone rubber which is then cured or dried. The filaments 22, 26, and 28 may be formed by wrapping continuous fiber about the covering mounted on a mandrel so that the pattern of wrapping is presented. Alternatively, the filaments may be knitted in a close-fitting sock arrangement, and disposed over a mandrel. This method provides for a full integration of the filament structure within a body of silicone rubber. The silicone rubber covering would be intimately adherent to the filaments.

Formation of Silicone Rubber Foam Using Electrically Charged Gas Bubbles

Figure 3:
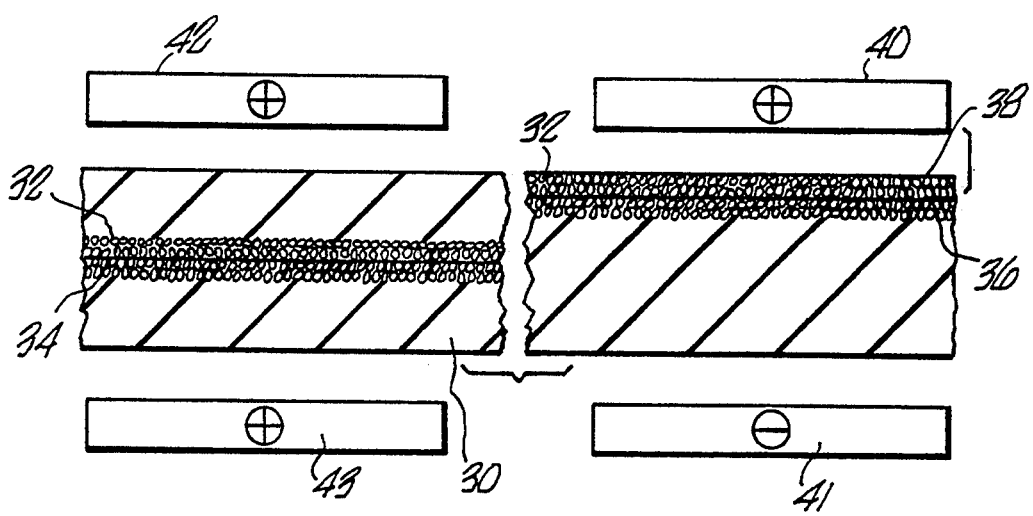
FIG. 3 is a cross-section of texturized silicone foam manufactured by the electrically charged bubble method.

FIG. 3 shows a silicone rubber foam structure, consisting of a generally solid silicone rubber portion 30 and bubble rich portions 32. The left hand portion of FIG. 3 shows the bubbles centrally disposed within the silicone rubber 30. The right hand portion of 33 shows the bubble rich region 32 disposed at the upper surface of the silicone 30. The silicone rubber foam is formed by exposing the bubble rich regions 32 to the exterior of the material. Taking the left hand side of FIG. 3, a cut along the line 34 will expose an open cell foam of silicone rubber. As to the right hand of FIG. 3, a cut along the line 36, or abrasion of the surface 38 would expose the bubble rich regions to generate the silicone foam.

In manufacture, the bubbles are preferably electrically charged. Once the charged bubbles are within the liquid silicone rubber 30, they may be positioned by application of an electric field, for example through use of an electrode 40.

I claim:

1. A method for forming a texturized coating for an implant comprising the steps of:
   affixing microtexturized globules onto a mandrel,
   coating the globules and mandrel with silicone rubber, curing the rubber, and
   removing the cured rubber from the mandrel and globules.

2. A method for forming a texturized coating for an implant comprising the steps of:
   affixing microtexturized globules to the inside of a mold;
   coating the globules and mold with silicone rubber, curing the rubber, and
   removing the cured rubber from the mold and globules.

3. The method for forming a texturized coating for an implant of claim 1 wherein the microtexturized globules are chosen from the following group: gold, platinum, tin, aluminum, brass, bronze and pyrex.

4. The method for forming a texturized coating for an implant of claim 1 wherein the globules are microtexturized by one of the following processes: sand blasting, etching, electrical discharge machining, ultrasonic impact machining, heat treating, super-cooled treating, laser machining, fracturing, ion beam distressing, and chemical leaching of calcareous inclusions.

5. The method for forming a texturized coating for an implant of claim 2 wherein the microtexturized globules are chosen from the following group: gold, platinum, tin, aluminum, brass, bronze and pyrex.

6. The method for forming a texturized coating for an implant of claim 2 wherein the globules are microtexturized by one of the following processes: sand blasting, etching, electrical discharge machining, ultrasonic impact machining, heat treating, super-cooled treating, laser machining, fracturing, ion beam distressing, and chemical leaching of calcareous inclusions.

* * * * *